US012491314B2

(12) United States Patent
Smith

(10) Patent No.: US 12,491,314 B2
(45) Date of Patent: Dec. 9, 2025

(54) DEVICE FOR TRANSFERRING AND CONDITIONING INFUSION LIQUID AND RELATED TECHNOLOGY

(71) Applicant: MEDTRONIC MINIMED, INC., Northridge, CA (US)

(72) Inventor: Roger E. Smith, Ivins, UT (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 764 days.

(21) Appl. No.: 17/663,620

(22) Filed: May 16, 2022

(65) Prior Publication Data

US 2023/0364336 A1 Nov. 16, 2023

(51) Int. Cl.

*A61M 5/168* (2006.01)
*A61M 5/14* (2006.01)
*A61M 5/165* (2006.01)

(52) U.S. Cl.

CPC ...... *A61M 5/16809* (2013.01); *A61M 5/1413* (2013.01); *A61M 5/165* (2013.01)

(58) Field of Classification Search

CPC .......... A61J 1/20; A61J 1/2003; A61J 1/2037; A61J 1/2062; A61J 1/2079; A61J 1/2086; A61J 1/2096; A61M 3/005; A61M 3/0283; A61M 5/165; A61M 5/3145; A61M 5/3294; A61M 5/345; A61M 5/38; A61M 5/385; A61M 2005/1652; A61M 2005/1655; A61M 2005/1657; A61M 2005/3114; A61M 2005/3128; A61M 39/10; A61M 2202/0028; A61M 2202/0042; A61M 2202/005; A61M 2202/0057

See application file for complete search history.

(56) References Cited

U.S. PATENT DOCUMENTS

| | | | | |
|---|---|---|---|---|
| 3,938,513 A * | 2/1976 | Hargest ............... | A61M 5/3145 | 604/190 |
| 4,332,249 A * | 6/1982 | Joslin .................... | A61M 39/24 | 604/36 |
| 4,391,274 A * | 7/1983 | Kagan ................... | A61M 5/165 | 604/247 |
| 6,796,965 B2 * | 9/2004 | Dumaresq-Lucas ......................... | A61M 5/3145 | 604/247 |

(Continued)

FOREIGN PATENT DOCUMENTS

| | | |
|---|---|---|
| CN | 103006437 A | 4/2013 |
| WO | 2016111400 A1 | 7/2016 |

*Primary Examiner* — Kami A Bosworth
(74) *Attorney, Agent, or Firm* — Fortem IP LLP

(57) ABSTRACT

A device in accordance with an embodiment of the present technology includes a port through which the device receives and dispenses infusion liquid (e.g., insulin solution) and a container that holds the infusion liquid. The device also includes a hub at a flowpath extending between the port and the container. The hub defines a first passage and a second passage in parallel with one another. The device further includes a conditioner and a check valve at the first and second passages, respectively. The conditioner conditions liquid moving between the container and the port by passing the liquid through an adsorbent filter and a mechanical filter. The check valve causes liquid moving between the port and the container to move preferentially via the first passage when flowing in one direction and to move preferentially via the second passage when flowing in an opposite direction.

20 Claims, 7 Drawing Sheets

(56) References Cited

U.S. PATENT DOCUMENTS

| | | | | |
|---|---|---|---|---|
| 2013/0116617 | A1* | 5/2013 | Martin ................ | A61M 5/3294 604/82 |
| 2013/0144222 | A1* | 6/2013 | Kawamura ....... | A61M 5/31531 604/228 |
| 2014/0171861 | A1* | 6/2014 | Stroumpoulis ..... | A61M 5/2448 604/85 |
| 2014/0213982 | A1* | 7/2014 | Kim ...................... | A61M 5/329 604/190 |
| 2014/0254303 | A1* | 9/2014 | McArthur ......... | A61M 5/31596 366/129 |
| 2016/0091399 | A1* | 3/2016 | Chen ................... | A61M 5/3145 73/863.23 |
| 2016/0256635 | A1* | 9/2016 | Kim .................... | A61M 5/3145 |
| 2018/0147359 | A1* | 5/2018 | Seok ................... | A61M 5/3145 |
| 2021/0128829 | A1* | 5/2021 | Novak .............. | A61M 5/14248 |
| 2021/0145697 | A1 | 5/2021 | Bourelle et al. | |

* cited by examiner

DEVICE FOR TRANSFERRING AND CONDITIONING INFUSION LIQUID AND RELATED TECHNOLOGY

TECHNICAL FIELD

This disclosure is related to transferring infusion liquid, such as from a storage reservoir to a portable reservoir of a wearable infusion device.

BACKGROUND

Infusion devices are used to control delivery of medication directly into a patient's bloodstream. In some cases, the delivery of medication from an infusion device is slow and continuous. This can be useful, for example, to maintain a steady concentration of medication in a patient's bloodstream over many hours or days. Infusion devices can also respond quickly (e.g., in near real time) to biometric information from associated sensors. A common use for infusion devices is in the treatment of diabetes. Many patients with diabetes benefit from frequent or continuous infusion of insulin. This need can be temporary, such as during a hospital admission, or long-term. In the latter case, wearable infusion devices can enable a patient to receive necessary insulin infusion therapy while maintaining an active lifestyle. Wearable infusion devices typically include a battery-powered pump, a reservoir, and a cannula. The cannula is maintained in a transcutaneous position at an infusion site, such as under an adhesive patch applied directly to a patient's skin. In some cases, the pump and reservoir are in a separate unit flexibly tethered to the cannula. This unit, for example, can be strapped to a patient or attached to a patient's clothing. Alternatively, the pump and reservoir can be integrated with the cannula into a single unit configured to be directly attached to a patient's skin at an infusion site.

Without modern infusion devices, management of diabetes and other conditions that require continuous or frequent infusion of medication would be far more problematic. For example, many patients suffering from diabetes have difficulty actively monitoring their need for insulin (e.g., by performing blood glucose tests) and responding to this need appropriately (e.g., by self-administering appropriate quantities of insulin). Without assistance, these patients can be subject to a significant, ongoing risk of serious complications including diabetic coma and death. Even when active disease management is within a patient's capabilities, it can be time-consuming and stressful. Infusion devices, therefore, not only save lives, they meaningfully improve the quality of life for patients with diabetes and other diseases. Given that diabetes affects hundreds of millions of people worldwide and is only one example of a disease that often requires continuous or frequent infusion of medication, the importance of infusion devices is difficult to overstate. Accordingly, there is an ongoing need for improvement of these devices. Even small improvements in this field can have major public health benefits.

SUMMARY

A transferring and conditioning device in accordance with at least some embodiments of the present technology includes a port through which the transferring and conditioning device is configured to receive and dispense liquid and a container at which the transferring and conditioning device is configured to hold liquid received via the port. The transferring and conditioning device also includes a flowpath extending between the port and the container and a hub at the flowpath. The hub includes a first passage, and a second passage in parallel with the first passage. The transferring and conditioning device further includes a conditioner at the first passage. The conditioner is configured to condition liquid moving between the port and the container via the first passage. The transferring and conditioning device still further includes a check valve at the second passage. The check valve is configured to cause liquid moving between the port and the container in a first direction to move preferentially via the first passage. The check valve is also configured to cause liquid moving between the port and the container in a second direction to move preferentially via the second passage, the second direction being opposite to the first direction.

An infusion system in accordance with at least some embodiments of the present technology includes a reservoir configured to contain infusion liquid and an infuser configured to deliver infusion liquid to a patient. The infusion system also includes a transferring and conditioning device configured to transfer infusion liquid from the reservoir to the infuser and to condition infusion liquid. The transferring and conditioning device includes a port through which the transferring and conditioning device is configured to receive infusion liquid from the reservoir and to dispense infusion liquid to the infuser and a container at which the transferring and conditioning device is configured to hold infusion liquid received via the port. The transferring and conditioning device also includes a flowpath extending between the port and the container and a conditioner at the flowpath. The conditioner is configured to condition infusion liquid moving between the port and the container.

A method for transferring and conditioning insulin solution in accordance with at least some embodiments of the present technology includes flowing insulin solution from a reservoir into a transferring and conditioning device. The method further includes flowing insulin solution from the transferring and conditioning device into an infuser. The method still further includes conditioning insulin solution at a conditioner of the transferring and conditioning device. The conditioning can be while flowing insulin solution from the reservoir into the transferring and conditioning device and/or while flowing insulin solution from the transferring and conditioning device into the infuser.

BRIEF DESCRIPTION OF THE DRAWINGS

Many aspects of the present technology can be better understood with reference to the following drawings. The relative dimensions in the drawings may be to scale with respect to some embodiments of the present technology. With respect to other embodiments, the drawings may not be to scale. The drawings may also be enlarged arbitrarily. For clarity, reference-number labels for analogous components or features may be omitted when the appropriate reference-number labels for such analogous components or features are clear in the context of the specification and all of the drawings considered together. Furthermore, the same reference numbers may be used to identify analogous components or features in multiple described embodiments.

DETAILED DESCRIPTION

Figure 1:
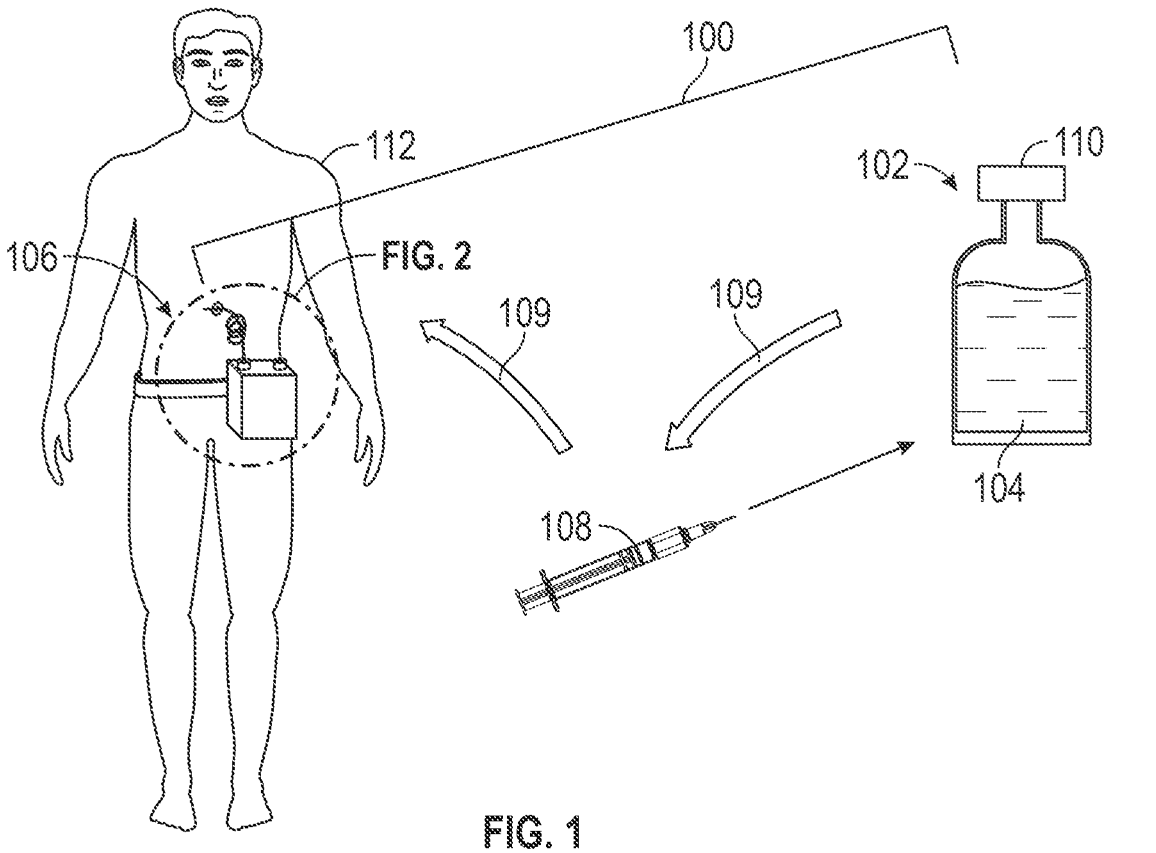
FIG. 1 is a perspective view of an infusion system in accordance with at least some embodiments of the present technology during treatment of a patient.

Devices for transferring and conditioning infusion liquid and related devices, systems, and methods in accordance with embodiments of the present technology at least partially address one or more problems associated with conventional technologies whether or not such problems are stated herein. Transferring and conditioning devices in accordance with at least some embodiments of the present technology include innovative features for prolonging the viability of infusion sites and thereby decreasing the need for creating new infusion sites. For example, these transferring and conditioning devices can condition infusion liquids and thereby reduce a tendency of the infusion liquids to promote inflammation, granulation, scarring, and/or other processes that tend to shorten infusion site viability. This conditioning can be in addition to or in place of conditioning closer in time to introduction of infusion liquid into a patient's bloodstream. For example, in methods for transferring and conditioning infusion liquid in accordance with some embodiments of the present technology, all conditioning occurs while transferring infusion liquid from a storage reservoir to an infuser. In other embodiments, some conditioning (e.g., rough conditioning) occurs at this stage whereas other conditioning (e.g., polish conditioning) occurs at the infuser. Conditioning at the infuser, for example, can occur as infusion liquid moves from a portable reservoir of the infuser to a transcutaneous cannula.

Infusion liquid held in a storage container may develop impurities, become contaminated, or otherwise degrade over time so as to become less compatible with prolonged infusion site viability. The rate at which this degradation occurs can be difficult to predict at least in part because it can depend on variable storage conditions, such as exposure to light, air, heat, and/or cold. Transferring and conditioning devices in accordance with at least some embodiments of the present technology remove material (e.g., an impurity) from and/or add material (e.g., a drug) to infusion liquid to counter at least some storage-related degradation and/or other degradation. In addition or alternatively, the conditioning can have other beneficial effects unrelated to degradation. For example, infusion liquid sometimes includes a preservative intended to reduce storage-related degradation. In the case of insulin solution, common preservatives include phenol and meta-cresol. These and other preservatives can be irritants that shorten infusion site viability and/or have other adverse effects. Conditioning in accordance with at least some embodiments of the present technology lowers a concentration of preservative in infusion liquid, thereby prolonging infusion site viability and/or having other beneficial effects. In these and other cases, it can be advantageous for conditioning to occur close in time with infusion, such as just before adding the infusion liquid to an infusion device, which will then be infused over the next several days (e.g., within 3, 5, or 10 days of infusion). Conditioning close in time with infusion may help to reduce the effect of subsequent degradation of the infusion liquid, which may occur relatively quickly when conditioning includes removing a preservative from the infusion liquid. In addition or alternatively, conditioning close in time with infusion may help to maintain the efficacy of any short-lived additives introduced during conditioning. In other cases, the beneficial effect of conditioning on infusion liquid can be more persistent.

Specific details of several embodiments of the present technology are disclosed herein with reference to FIGS. 1-9. It should be noted, in general, that other embodiments in addition to those disclosed herein are within the scope of the present technology. For example, embodiments of the present technology can have different configurations, components, and/or operations than those disclosed herein. Moreover, a person of ordinary skill in the art will understand that embodiments of the present technology can have configurations, components, and/or operations in addition to those disclosed herein and that these and other embodiments can be without configurations, components, and/or operations disclosed herein without deviating from the present technology.

FIG. 1 is a perspective view of an infusion system 100 in accordance with at least some embodiments of the present technology. The infusion system 100 can include a reservoir 102 configured to contain infusion liquid 104 (e.g., insulin solution), an infuser 106, and a transferring and conditioning device 108 configured to transfer infusion liquid 104 from the reservoir 102 to the infuser 106 and to condition the transferred infusion liquid 104. Arrows 109 indicate a path of the infusion liquid 104 from the reservoir 102, to the transferring and conditioning device 108, and then to the infuser 106. The reservoir 102 can be a vial or another suitable container having a cap 110. The infuser 106 can be configured to deliver infusion liquid 104 transferred from the reservoir 102 to a patient 112.

Figure 2:
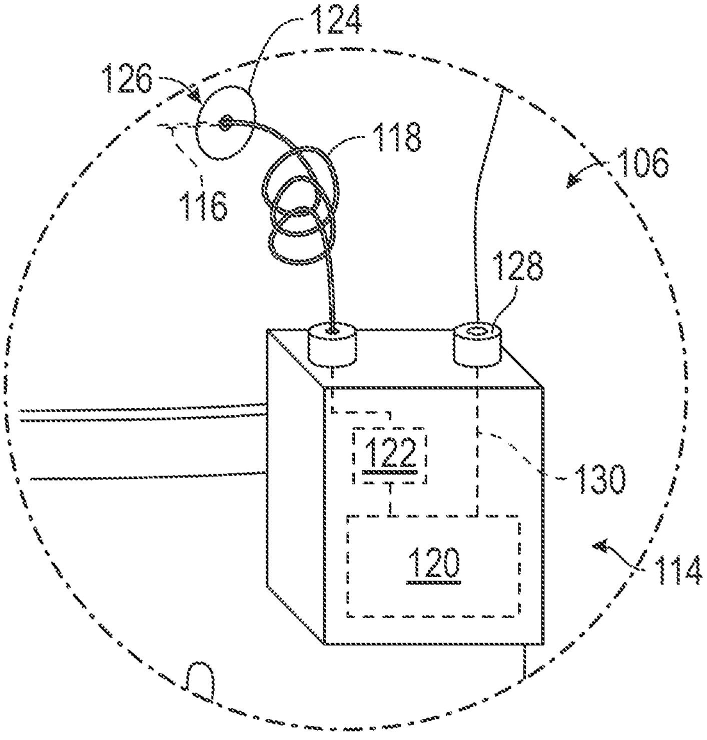
FIG. 2 is an enlarged view of portion of FIG. 1.

FIG. 2 is an enlarged view of portion of FIG. 1. With reference to FIGS. 1 and 2 together, the infuser 106 can include a main unit 114, a cannula 116, and a flexible tube 118 extending therebetween. Within the main unit 114, the infuser 106 can include a tank 120 configured to store infusion liquid 104 and a pump 122 configured to pump infusion liquid 104 from the tank 120 into the patient 112 via the tube 118 and the cannula 116. An adhesive patch 124 can be used to secure the cannula 116 in a transcutaneous position at an infusion site 126 on the patient 112. Although not shown in FIGS. 1 and 2, the infuser 106 can also include suitable control, sensor, and/or display components configured to regulate operation of the pump 122, to gather biometric information (e.g., blood glucose concentration), to indicate whether the tank 120 requires replenishment, and/or to perform other useful functions related to operation of the infuser 106.

In at least some cases, the infuser 106 is portable. For example, the infuser 106 can be wearable and can include a battery (not shown) that powers the pump 122. In other cases, the infuser 106 can be stationary. For example, a counterpart of the main unit 114 can be a bedside device for use in a hospital or home-care setting. When the infuser 106 is portable and in other cases, the tank 120 can have a capacity smaller than a capacity of the reservoir 102. Accordingly, it can be useful to transfer infusion liquid 104 from the reservoir 102 to the infuser 106 via the transferring and conditioning device 108 to replenish the tank 120 as needed. It can also be useful to transfer infusion liquid 104 from the reservoir 102 to the infuser 106 via the transferring and conditioning device 108 for other reasons, such as to initially fill the tank 120 or to change out the contents of the tank 120. To facilitate the occasional introduction of infusion liquid 104 into the tank 120, the main unit 114 can include an inlet 128 and a flowpath 130 extending between the inlet 128 and the tank 120. In other embodiments, the tank 120 may be a replaceable cartridge that is filled separately and inserted into the infuser 106.

The transferring and conditioning device 108 is further discussed below in detail with reference to FIGS. 3-8 in the context of the infusion system 100. It should be understood, however, that the transferring and conditioning device 108 and its counterparts can be used in a wide variety of infusion and other systems in addition to the system 100. For example, the transferring and conditioning device 108 can be used to transfer (e.g., apportion) and condition liquid medication for oral administration. As another example, the transferring and conditioning device 108 can be used to transfer and condition liquid reactants in a chemical reactor. As yet another example, the transferring and conditioning device 108 can be used to transfer and condition liquid medication injected directly into a patient 112 without the use of an infuser 106, such as with a multiple daily injector pen in the case of insulin delivery.

Figure 3:
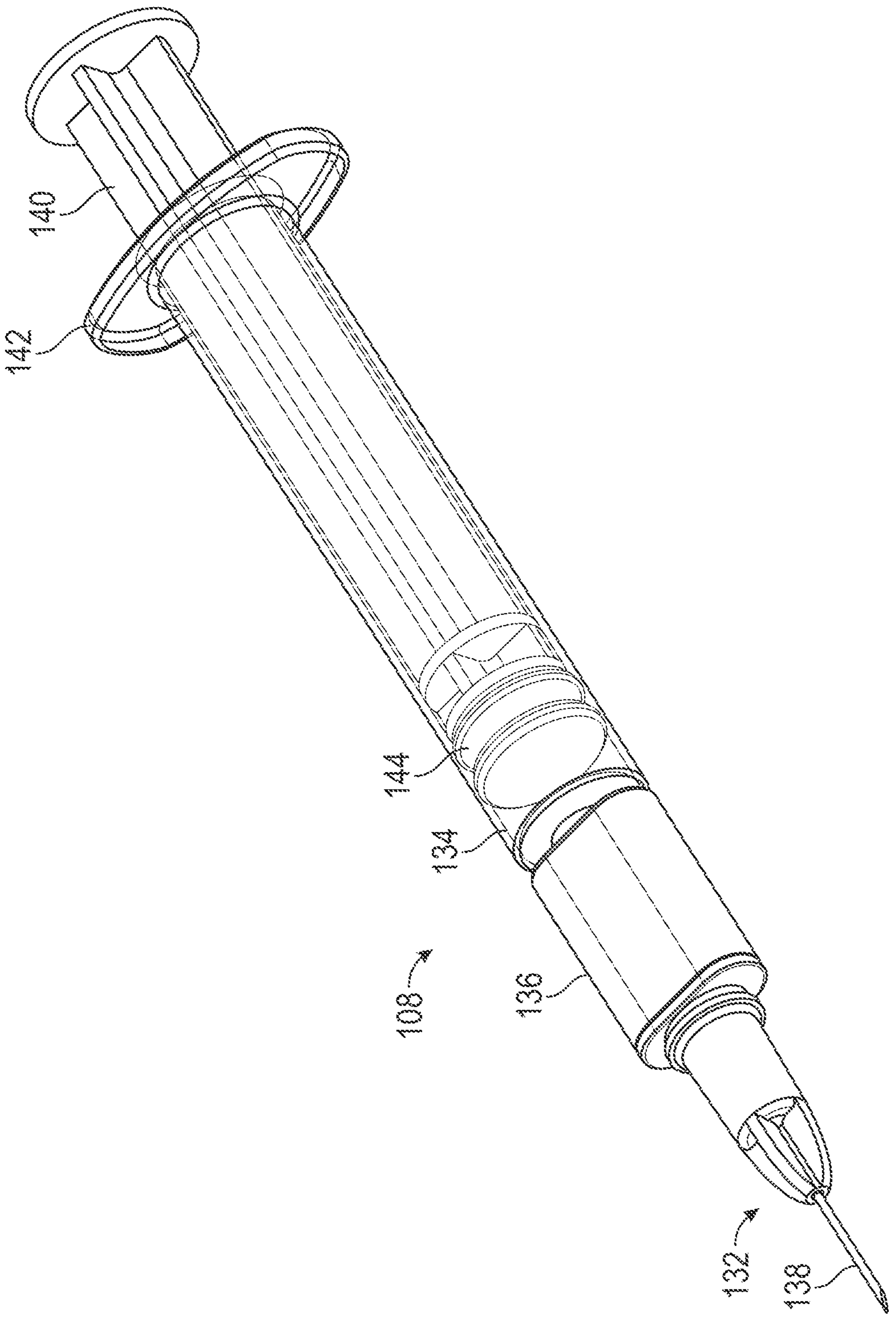
FIG. 3 is a perspective view of a transferring and conditioning device of the infusion system shown in FIG. 1.
Figure 4:
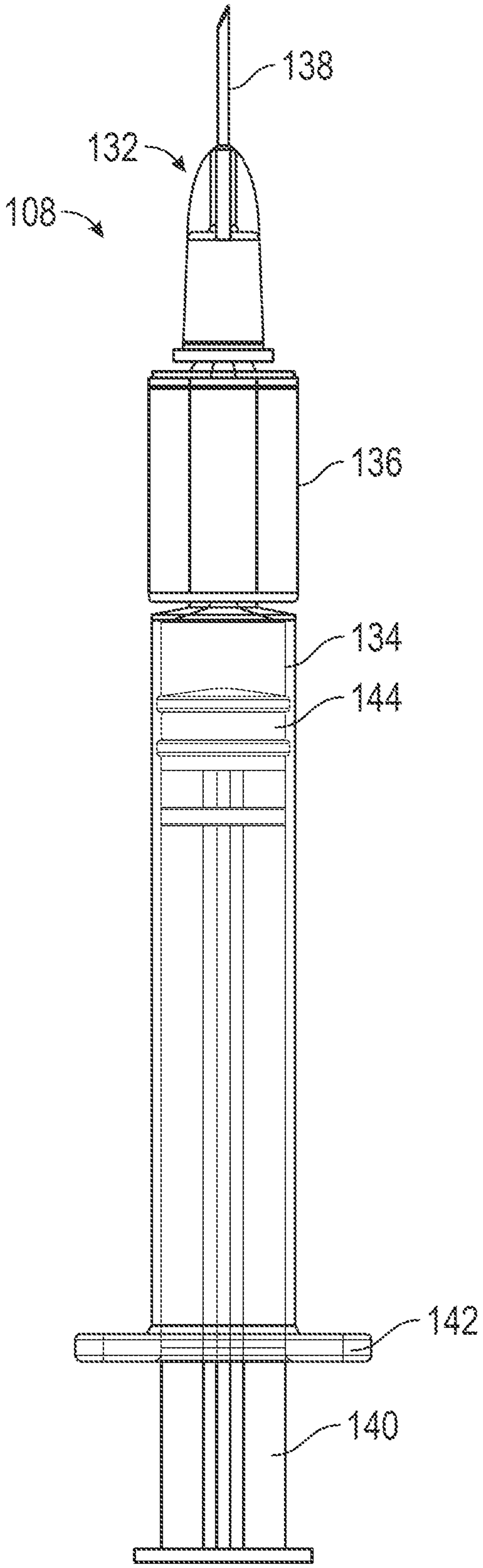
FIG. 4 is a top plan view of the transferring and conditioning device of the infusion system shown in FIG. 1.
Figure 5:
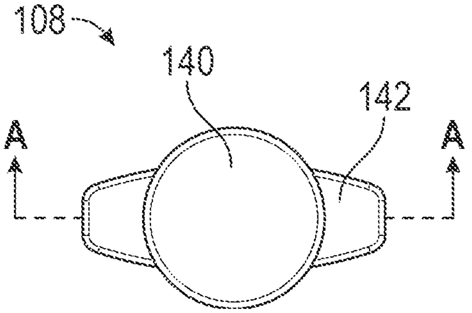
FIG. 5 is an end profile view of the transferring and conditioning device of the infusion system shown in FIG. 1.

FIGS. 3, 4 and 5 are a perspective view, a top plan view, and an end profile view, respectively, of the transferring and conditioning device 108. With reference to FIGS. 3-5 together, the transferring and conditioning device 108 can include a port 132 through which the transferring and conditioning device 108 is configured to receive and dispense liquid, a container 134 at which the transferring and conditioning device is configured to hold liquid received via the port 132, and a hub 136 therebetween. In at least some cases, the port 132 includes a needle 138. The needle 138 can be configured to penetrate the cap 110 of the reservoir 102 (FIG. 1) and the inlet 128 of the infuser 106 (FIG. 2). The transferring and conditioning device 108 can also include a plunger 140 slidingly disposed within the container 134. At an end of the container 134 farthest from the port 132, the transferring and conditioning device 108 can include a grip 142. The grip 142 can be used as a counterbalance when moving the plunger 140 relative to the container 134. The container 134 and the grip 142 can be made of transparent material (e.g., clear plastic), which can be useful, for example to permit a user of the transferring and conditioning device 108 to visually determine how much liquid is present in the container 134. As shown in FIGS. 3 and 4, the plunger 140 can include a stopper 144 that resiliently engages an inner wall of the container 134. Moving the plunger 140 axially within the container 134 can move the stopper 144 and thereby change an available volume within the container 134 and/or a pressure within the container 134.

The transferring and conditioning device 108 can be handheld. Relatedly, the container 134 can have a relatively small maximum capacity, such as a maximum capacity within a range from 0.05 to 100 ml or from 0.05 to 50 ml. Furthermore, the container 134 can be elongate, cylindrical, and axially aligned with the hub 136 and the port 132. In the illustrated embodiment, the transferring and conditioning device 108 has the general form of a syringe. The transferring and conditioning device 108 is configured such that a user of the transferring and conditioning device 108 can hold the container 134 in one hand and pull the plunger 140 with the other hand to draw liquid into the container 134 via the port 132. Using one hand or two, the user can then push the plunger 140 to move liquid out of the container 134 via the hub 136 and the port 132. The grip 142 can be used to stabilize the transferring and conditioning device 108 during these operations. In other embodiments, the transferring and conditioning device 108 can have other suitable forms, sizes, and/or operational features.

Figure 6:
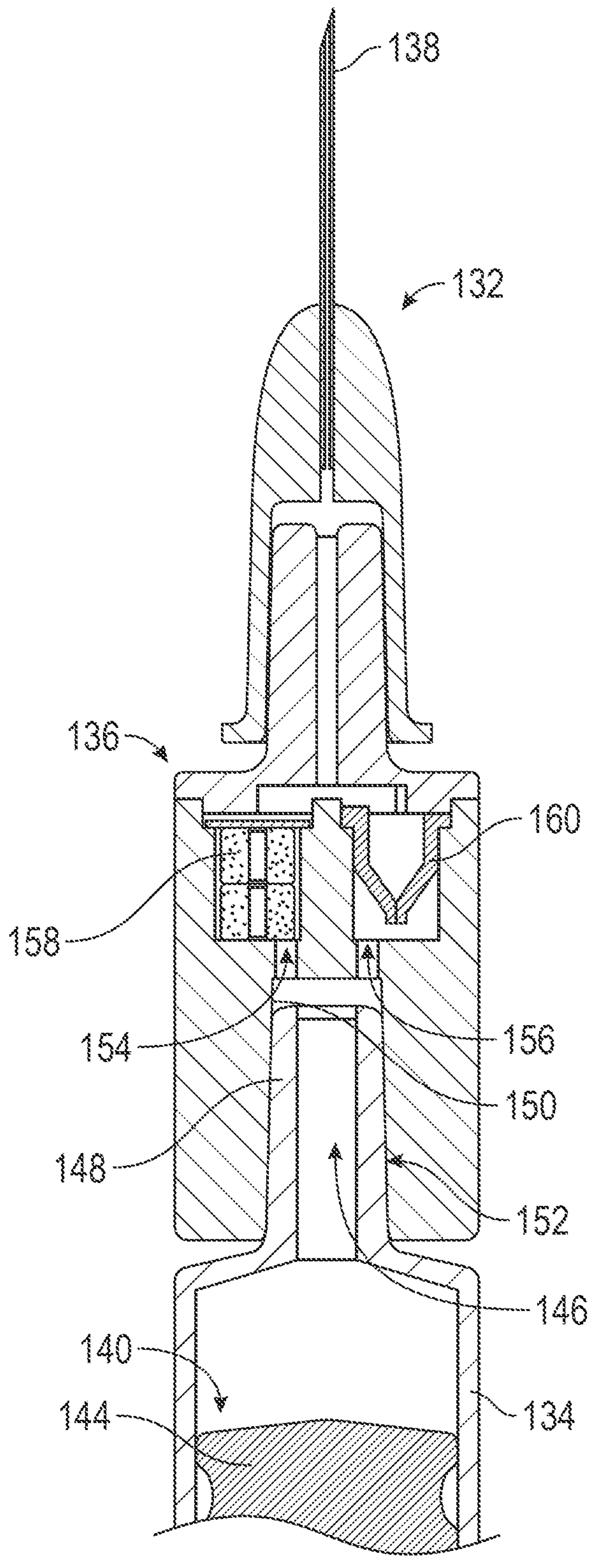
FIG. 6 is a partial cross-sectional top plan view taken along the line A-A in FIG. 5 of the transferring and conditioning device of the infusion system shown in FIG. 1.

FIG. 6 is a partial cross-sectional top plan view taken along the line A-A in FIG. 5 of the transferring and conditioning device 108. As shown in FIG. 6, the transferring and conditioning device 108 can include a flowpath 146 extending between the port 132 and the container 134. The transferring and conditioning device 108 can further include a stem 148 downstream from the container 134 with respect to liquid moving from the container 134 to the port 132. The flowpath 146 can extend through the stem 148. In at least some cases, the stem 148 is tapered inwardly along a portion of the flowpath 146 extending through the stem 148 from the container 134 toward the port 132. The hub 136 can likewise be located at the flowpath 146. The hub 136 can define a recess 150 configured to receive the stem 148. For example, the recess 150 can be tapered inwardly along the portion of the flowpath 146 extending through the stem 148 from the container 134 toward the port 132. In these and other cases, the container 134 can be detachable from the hub 136. For example, the transferring and conditioning device 108 can include a seal 152 between the container 134 and the hub 136 (e.g., between the stem 148 and the recess 150) at which container 134 can be slidingly or otherwise separated from the hub 136. In some embodiments, the stem 148 and the recess 150 may have mating threads to removably engage the hub 136 to the container 134. Alternatively, the container 134 can be hermetically welded or otherwise fixedly connected to the hub 136 at an interface between the stem 148 and the recess 150.

The hub 136 can define a first passage 154 and a second passage 156 in parallel with the first passage 154. The hub 136 can be configured, for example, such that an unseparated quantity of liquid can flow between the container 134 and the port 132 via the first passage 154 or alternatively via the second passage 156. The transferring and conditioning device 108 can include a conditioner 158 at the first passage 154 and a check valve 160 at the second passage 156. The conditioner 158 can be configured to condition liquid moving between the container 134 and the port 132 and via the first passage 154. In the illustrated embodiment, the check valve 160 is an elastomeric duckbill valve. In other embodiments, counterparts of the check valve 160 can have other suitable forms. For example, a counterpart of the check valve 160 can be a diaphragm valve, a butterfly valve, or a ball valve. These and other suitable types of check valves can be spring-assisted or passive.

The check valve 160 can be configured to permit or inhibit flow of liquid through the second passage 156 depending on a direction of the flow. In contrast, flow across the conditioner 158 can be relatively independent of direction. A pressure drop across the conditioner 158 with respect to liquid flowing from the port 132 to the container 134 via the first passage 154 can be significantly greater (e.g., over five times greater) than a pressure drop across the check valve 160 with respect to liquid flowing from the port 132 to the container 134 via the second passage 156. Accordingly, the transferring and conditioning device 108 can be configured such that sliding the plunger 140 away from the hub 136 moves liquid from the port 132 to the container 134 preferentially via the second passage 156. In contrast, a pressure drop across the conditioner 158 with respect to liquid flowing from the container 134 to the port 132 via the first passage 154 can be significantly lower (e.g., over five times lower) than a backflow burst pressure of the check valve 160. Accordingly, the transferring and conditioning device 108 can be configured such that sliding the plunger 140 toward the hub 136 moves liquid from the container 134 to the port 132 preferentially via the first passage 154.

Figure 7:
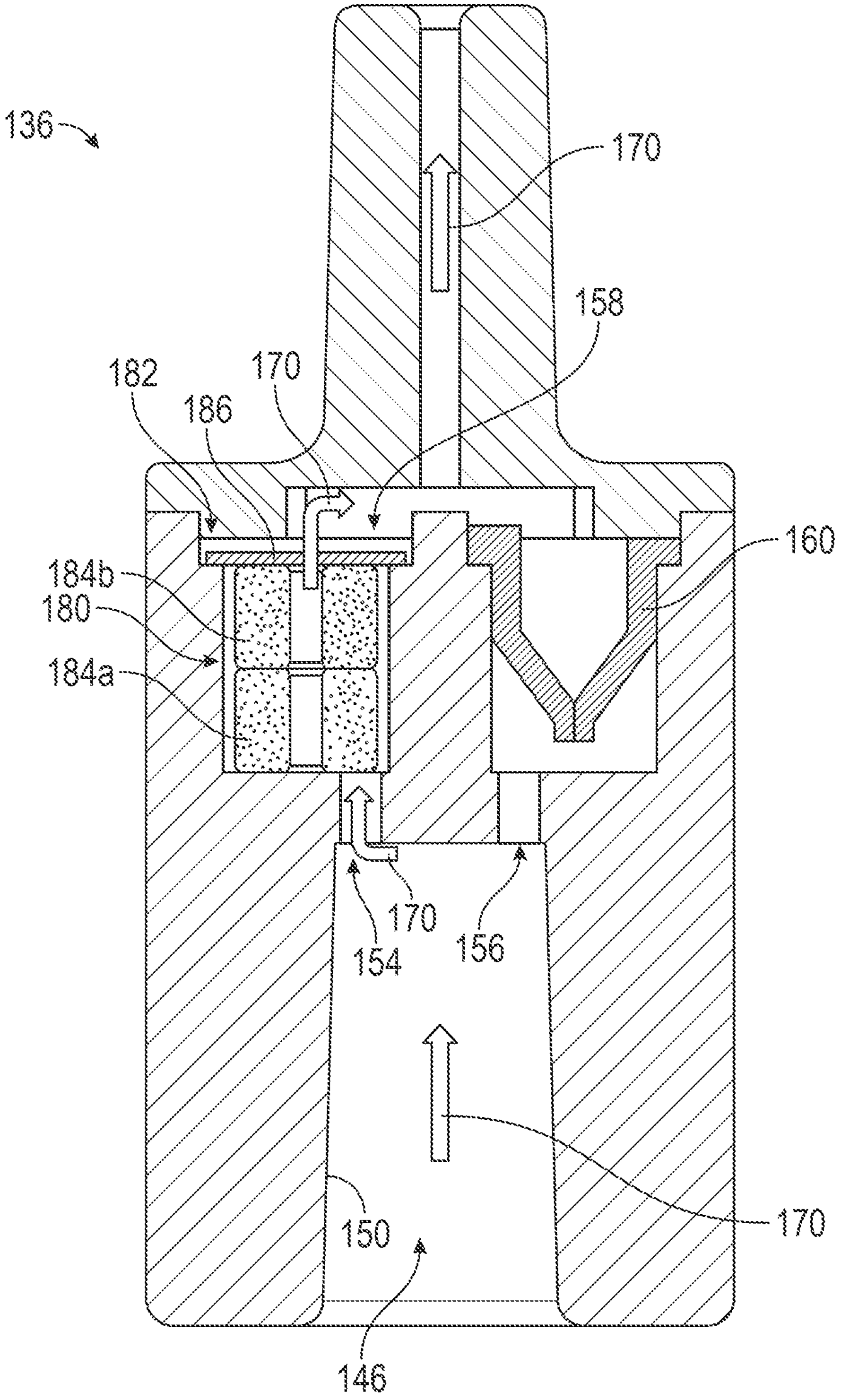
FIG. 7 is a partial cross-sectional top plan view taken along the line A-A in FIG. 5 of the transferring and conditioning device of the infusion system shown in FIG. 1 in a dispensing state.
Figure 8:
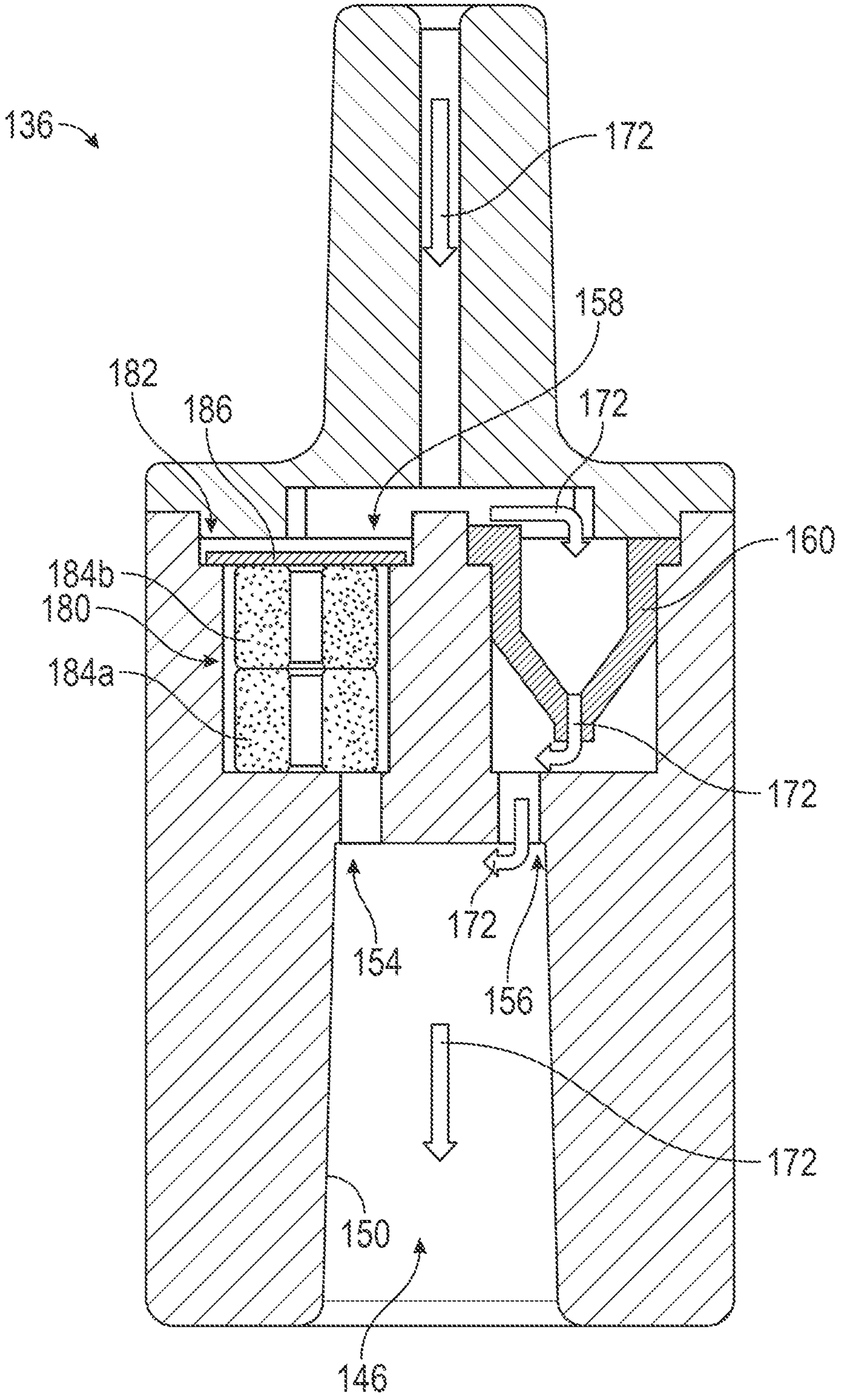
FIG. 8 is a partial cross-sectional top plan view taken along the line A-A in FIG. 5 of the transferring and conditioning device of the infusion system shown in FIG. 1 in a filling state.

FIG. 7 is a cross-sectional top plan view taken along the line A-A in FIG. 5 of the hub 136 while the transferring and conditioning device 108 is in a dispensing state. With reference to FIGS. 6 and 7 together, the check valve 160 can be configured to cause liquid moving between the container 134 and the port 132 in a first direction indicated by arrows 170 to move preferentially via the first passage 154 while the transferring and conditioning device 108 is in the dispensing state. FIG. 8 is a cross-sectional top plan view taken along the line A-A in FIG. 5 of the hub 136 while the transferring and conditioning device 108 is in a filling state. With reference to FIGS. 6 and 8 together, the check valve 160 can be configured to cause liquid moving between the port 132 and the container 134 in a second direction indicated by arrows 172 to move preferentially via the second passage 156 while the transferring and conditioning device 108 is in the filling state.

As shown in FIGS. 7 and 8, the first direction indicated by arrows 170 is opposite to the second direction indicated by arrows 172. In the illustrated embodiment, the first direction is from the container 134 to the port 132 and the second direction is from the port 132 to the container 134. In some cases, it is useful for the check valve 160 to cause liquid to move preferentially through the conditioner 158 in response to pushing the plunger 140 because this action tends to be more forceful and sustainable than pulling the plunger 140. In other cases, however, the first and second directions can be switched. For example, a counterpart of the check valve 160 can be flipped such that it is configured to cause liquid moving from the port 132 to the container 134 to move preferentially via the first passage 154 and to cause liquid moving from the container 134 to the port 132 to move preferentially via the second passage 156, which will condition the liquid as it enters the transferring and conditioning device 108.

The conditioner 158 can include one, two, three, or more conditioning stages. For example, as most clearly shown in FIGS. 7 and 8, the conditioner 158 can include a first stage 180 and a second stage 182. The first stage 180 can be upstream from the second stage 182 with respect to liquid flowing through the first passage 154 from the container 134 to the port 132. In at least some cases, a pressure drop across the second stage 182 is greater (e.g., at least three times greater) than a pressure drop across the first stage 180 with respect to liquid flowing through the first passage 154 from the container 134 to the port 132. Due to the presence of the second stage 182 at the first passage 154 (whether upstream or downstream from the first stage 180), a residence time of liquid at the first stage 180 for a given motive pressure differential between the container 134 and the port 132 can be greater than if the second stage 182 was absent. This can be useful, for example, to enable the first stage 180 sufficient time to condition liquid even when the motive pressure differential between the container 134 and the port 132 is high and the pressure drop across the first stage 180 is low. Thus, the second stage 182 can act as a flow regulator in addition to or instead of having a separate conditioning function.

In some cases, the conditioner 158 is configured to condition insulin solution. Such conditioning can be useful, for example, to prolong infusion site viability and thereby decrease the need for creating new infusion sites. For example, conditioning insulin solution at the conditioner 158 can reduce a tendency of insulin solution to promote inflammation, granulation, scarring, and/or other processes that tend to shorten infusion site viability. The conditioner 158 can be configured to remove material from, add material to, or otherwise change the properties of insulin solution. Examples of material that can be removed from insulin solution at the conditioner 158 include air, aggregates (e.g., amyloid fibrils), and contaminants (e.g., dust). Examples of material that can be added to insulin solution at the conditioner 158 include anticoagulants (e.g., heparin), anti-inflammatories, and other drugs that can reduce inflammation, granulation, scarring, and/or other processes that tend to shorten infusion site viability.

As shown in FIGS. 7 and 8, the first stage 180 can include an adsorbent filter in the form of annular plugs 184 (individually identified as plugs 184*a*-184*b*) of porous adsorbent media. Suitable types of porous adsorbent media include crosslinked polyvinyl alcohol (PVA), cellulose, polyurethane, polyester, polyether, and collagen, among others. The porous adsorbent media can have one or more of the following properties: (a) an average pore size within a range from 0.1 to 5 mm (e.g., from 0.3 to 1 mm), (b) a porosity within a range from 50% to 95% (e.g., from 90% to 95%), (c) a dry density within a range from 0.1 to 1.5 grams per cubic inch (e.g., from 0.8 to 1.5 grams per cubic inch), (d) absorption of water to 95% saturation within a range from 6 to 60 seconds (e.g., from 3 and 30 seconds), and (e) maximum retention of liquid insulin solution within a range from 5 to 100 times dry weight (e.g., from 10 to 25 times dry weight). In addition to or instead of both annular plugs 184, a counterpart of the first stage 180 can include a release mechanism (e.g., in some embodiments replacing annular plug 184*b*) configured to gradually release a drug (e.g., heparin) or another substance into liquid at the first passage 154. Examples of suitable release mechanisms include drug-infused polymer matrices that limit drug release by solubility and membrane encapsulated drug suspensions that limit drug release by diffusion, among others.

As also shown in FIGS. 7 and 8, the second stage 182 can include a mechanical filter 186, such as a membrane filter. The mechanical filter 186 can be polymeric. In these and other cases, the mechanical filter 186 can have an average pore size within a range from 0.1 to 10 μm. Examples of suitable materials for the mechanical filter 186 include: (a) acrylic copolymer with an average pore size within a range from 0.1 to 10 μm, (b) polyethersulfone with an average pore size within a range from 0.1 to 10 μm, (c) mixed cellulose esters with an average pore size within a range from 0.1 to 10 μm, (d) cellulose acetate with an average pore size within a range from 0.1 to 10 μm, (e) cellulose nitrate with an average pore size within a range from 0.1 to 10 μm, (f) nylon with an average pore size within a range from 0.21 to 10 μm, (g) hydrophilic polytetrafluoroethylene (PTFE) with an average pore size within a range from 0.1 to 10 μm, and (h) polycarbonate with an average pore size within a range from 0.1 to 10 μm.

Figure 9:
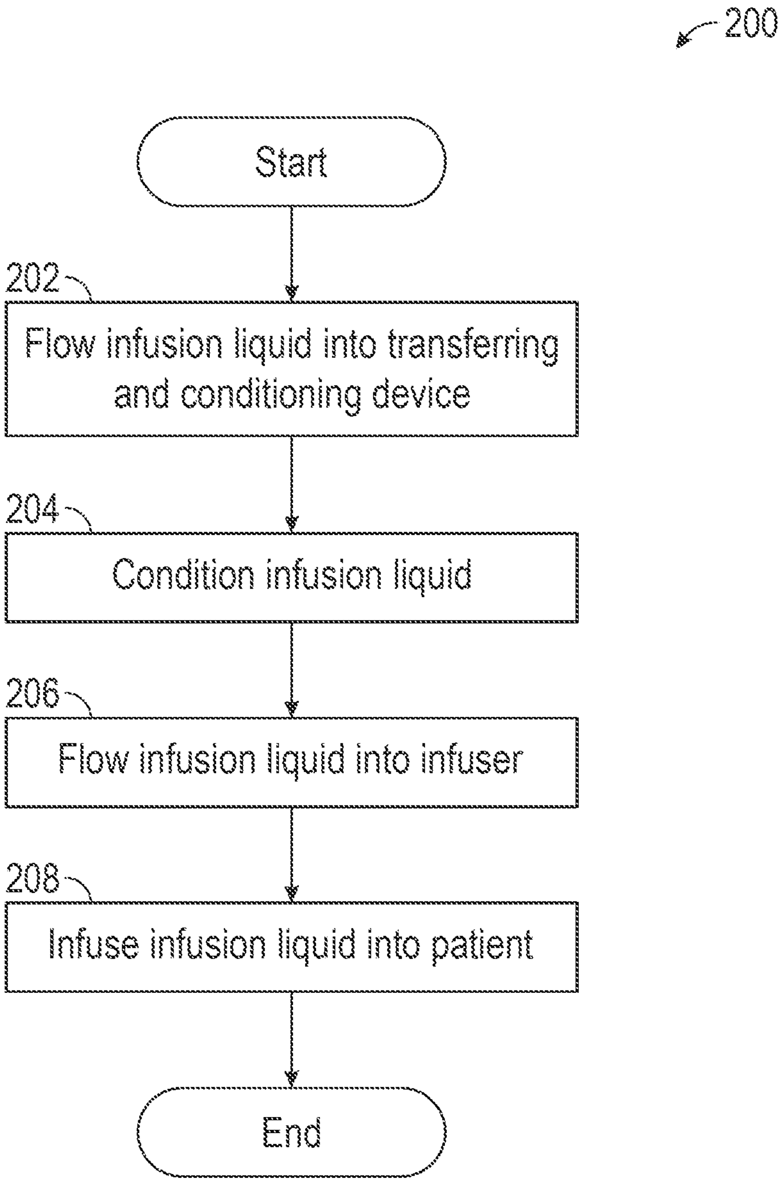
FIG. 9 is a block diagram illustrating a method for transferring and conditioning infusion liquid in accordance with at least some embodiments of the present technology.

FIG. 9 is a block diagram illustrating a method 200 for transferring and conditioning infusion liquid, such as insulin solution, in accordance with at least some embodiments of the present technology. For simplicity, aspects of the method 200 will be further described primarily in the context of the infusion system 100 described herein. It should be understood, however, that the method 200, when suitable, and/or portions of the method 200, when suitable, can be practiced with respect to other systems in accordance with embodiments of the present technology.

With reference to FIGS. 1-9 together, the method 200 can include flowing infusion liquid 104 from the reservoir 102 into the transferring and conditioning device 108 (block 202). This can include inserting the needle 138 into the cap 110 and pulling the plunger 140 to draw infusion liquid 104 into the container 134 via the port 132 and the check valve 160. The check valve 160 can cause infusion liquid 104 moving from the port 132 to the container 134 to preferentially bypass the conditioner 158. For example, at least 90% by volume (e.g., at least 95% by volume) of infusion liquid 104 moving from the port 132 to the container 134 can flow through the check valve 160 at the second passage 156.

The method 200 can further include conditioning infusion liquid 104 at the conditioner 158 (block 204). The conditioning can occur while flowing infusion liquid 104 from the reservoir 102 into the transferring and conditioning device 108, such as while flowing infusion liquid 104 from the reservoir 102 into the container 134 via the port 132. Alternatively or in addition, the conditioning can occur while flowing infusion liquid 104 from the transferring and conditioning device 108 to the infuser 106, such as while flowing infusion liquid 104 from the container 134 to the infuser 106 via the port 132. For example, in a counterpart of the transferring and conditioning device 108, the orientation of the check valve 160 can be reversed. Conditioning infusion liquid 104 can include flowing infusion liquid 104 through the mechanical filter 186 and/or through an adsorbent filter (e.g., the annular plugs 184). When the infusion liquid 104 is insulin solution and in other cases, conditioning the infusion liquid 104 can include removing air, removing aggregates, removing preservative, and/or releasing a drug.

Next, the method 200 can include flowing infusion liquid 104 from the transferring and conditioning device 108 into the infuser 106 (block 206) and finally infusing infusion liquid 104 into the patient 112 (block 208). When the infusion liquid 104 is insulin solution and in other cases, infusing the infusion liquid 104 can occur relatively soon after conditioning the infusion liquid (e.g., within 6 days, within 8 days, or within 10 days). In some cases, a given quantity of infusion liquid 104 is conditioned both at the transferring and conditioning device 108 and at the infuser 106. For example, conditioning at the transferring and conditioning device 108 can be of a type (e.g., removing aggregates) that has a longer duration of effectiveness, whereas conditioning at the infuser 106 can be of a type (e.g., removing air) that has a shorter duration of effectiveness. In other cases, conditioning occurs at the transferring and conditioning device 108 and does not occur at the infuser 106. Conditioning a quantity of infusion liquid 104 (e.g., insulin solution) at the transferring and conditioning device 108 can meaningfully increase a viability of the infusion site 126 relative to a control in which a corresponding quantity of infusion liquid 104 is not conditioned. The period of increase, for example, can be at least one day, such as within a range from one to three days. For example, increasing the use of an infusion site from three days to five days decreases the number of infusion site changes from 121 times a year to 73 times a year (48 less infusion site changes per year). That translates to, in the case of a tethered insulin infusion pump, 48 less infusion sets used, which is a benefit to the patient both in convenience and cost, and a benefit to the environment of less infusion sets disposed.

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may be disclosed herein in the context of those embodiments, other embodiments may also exhibit such advantages, and not all embodiments need necessarily exhibit such advantages or other advantages disclosed herein to fall within the scope of the present technology. This disclosure and the associated technology can encompass other embodiments not expressly shown or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising," "including," and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various structures. It should be understood that such terms do not denote absolute orientation. Furthermore, reference herein to "one embodiment," "an embodiment," or similar phrases means that a particular feature, structure, operation, or characteristic described in connection with such phrases can be included in at least one embodiment of the present technology. Thus, such phrases as used herein are not necessarily all referring to the same embodiment. Finally, it should be noted that various particular features, structures, operations, and characteristics of the embodiments described herein may be combined in any suitable manner in additional embodiments in accordance with the present technology.

I claim:

1. A transferring and conditioning device, comprising:
a port through which the transferring and conditioning device is configured to receive and dispense a liquid;
a container configured to hold the liquid received via the port;
a flowpath extending between the port and the container;
a hub through which the flowpath extends, wherein the hub defines:
a first passage, and
a second passage in parallel with the first passage;

a conditioner at the first passage, wherein the conditioner is configured to condition the liquid moving between the port and the container via the first passage; and a check valve at the second passage, wherein the check valve is configured:

to cause the liquid moving between the port and the container in a first direction to move preferentially via the first passage, and to cause the liquid moving between the port and the container in a second direction to move preferentially via the second passage, wherein the second direction is opposite to the first direction, wherein a pressure drop across the conditioner with respect to the liquid moving in the second direction is greater than a pressure drop across the check valve with respect to the liquid moving in the second direction.

2. The transferring and conditioning device of claim 1, wherein the check valve is configured:

to cause the liquid moving from the container to the port to move preferentially via the first passage; and to cause the liquid moving from the port to the container to move preferentially via the second passage.

3. The transferring and conditioning device of claim 1, wherein the port includes a needle.

4. The transferring and conditioning device of claim 1, wherein the container has a maximum capacity within a range from 0.05 ml to 50 ml.

5. The transferring and conditioning device of claim 1, further comprising a plunger slidingly disposed within the container, wherein:

the transferring and conditioning device is configured such that sliding the plunger away from the hub moves the liquid from the port to the container preferentially via the second passage; and the transferring and conditioning device is configured such that sliding the plunger toward the hub moves the liquid from the container to the port preferentially via the first passage.

6. The transferring and conditioning device of claim 1, wherein the pressure drop across the conditioner with respect to the liquid moving in the second direction is at least five times greater than a pressure drop across a check valve with respect to the liquid moving in the second direction.

7. The transferring and conditioning device of claim 1, wherein the container and the hub form a seal therebetween, and wherein the container is detachable from the hub at the seal.

8. The transferring and conditioning device of claim 1, wherein a stem at a downstream end of the container with respect to the liquid moving from the container to the port is configured such that:

the hub defines a recess configured to receive the stem; and the recess and the stem are tapered inwardly along a portion of the flowpath extending through the stem from the container toward the port.

9. The transferring and conditioning device of claim 1, wherein:

the conditioner includes a first stage and a second stage; and a pressure drop across the second stage is greater than a pressure drop across the first stage with respect to the liquid flowing through the first passage.

10. The transferring and conditioning device of claim 9, wherein the first stage includes a release mechanism configured to gradually release a drug into the liquid flowing through the first passage.

11. The transferring and conditioning device of claim 9, wherein:

the first stage includes an adsorbent filter; and the second stage includes a mechanical filter.

12. The transferring and conditioning device of claim 9, wherein the pressure drop across the second stage with respect to the liquid flowing through the first passage is at least three times greater than the pressure drop across the first stage with respect to the liquid flowing through the first passage.

13. An infusion system, comprising:

a reservoir configured to contain infusion liquid;

an infuser configured to deliver the infusion liquid to a patient; and a transferring and conditioning device configured to transfer the infusion liquid from the reservoir to the infuser and to condition the infusion liquid, wherein the transferring and conditioning device includes:

a port through which the transferring and conditioning device is configured to receive the infusion liquid from the reservoir and to dispense the infusion liquid to the infuser, a container configured to hold the infusion liquid received via the port;

a flowpath extending between the port and the container, wherein the flowpath comprises a first passage and a second passage, wherein the second passage is in parallel with the first passage;

a conditioner along the flowpath at the first passage, wherein the conditioner is configured to condition the infusion liquid moving between the port and the container; and a check valve at the second passage, wherein the check valve is configured to cause the infusion liquid moving from the port to the container to drop in pressure across the first passage and the second passage, and wherein the pressure drop across the first passage is greater than the pressure drop across the second passage.

14. The infusion system of claim 13, wherein the transferring and conditioning device is handheld.

15. The infusion system of claim 13, wherein the conditioner includes a mechanical filter.

16. The infusion system of claim 13, wherein the conditioner includes an adsorbent filter.

17. The infusion system of claim 13, wherein the conditioner includes a release mechanism configured to gradually release a drug into the infusion liquid at the conditioner.

18. The infusion system of claim 13, wherein:

the conditioner includes a first stage and a second stage;

a pressure drop across the second stage is at least three times greater than a pressure drop across the first stage; and the first stage includes one or both of an adsorbent filter and a release mechanism configured to gradually release a drug into the infusion liquid at the conditioner.

19. The infusion system of claim 13, wherein:

the transferring and conditioning device includes a hub through which the flowpath extends;

the hub defines:

the first passage, and the second passage in parallel with the first passage; and wherein the check valve is configured:

to cause the infusion liquid moving between the port and the container in a first direction to move preferentially via the first passage, and to cause the infusion liquid moving between the port and the container in a second direction to move preferentially via the second passage, wherein the second direction is opposite to the first direction.

20. The infusion system of claim 19, wherein the check valve is configured:

to cause the infusion liquid moving from the container to the port to move preferentially via the first passage; and to cause the infusion liquid moving from the port to the container to move preferentially via the second passage.

* * * * *